(12) United States Patent
Inskeep

(10) Patent No.: US 8,581,522 B2
(45) Date of Patent: Nov. 12, 2013

(54) COUNTERTOP DECONTAMINATING DEVICE

(76) Inventor: Mathew Inskeep, Boca Raton, FL (US)

( * ) Notice: Subject to any disclaimer, the term of this patent is extended or adjusted under 35 U.S.C. 154(b) by 883 days.

(21) Appl. No.: 12/562,676

(22) Filed: Sep. 18, 2009

(65) Prior Publication Data
US 2010/0097013 A1 Apr. 22, 2010

Related U.S. Application Data

(60) Provisional application No. 61/098,535, filed on Sep. 19, 2008.

(51) Int. Cl.
H05B 37/02 (2006.01)

(52) U.S. Cl.
USPC .......................... 315/360; 315/149

(58) Field of Classification Search
USPC .......... 315/149, 360; 362/236, 246, 249, 363, 362/800, 806
See application file for complete search history.

(56) References Cited

U.S. PATENT DOCUMENTS

| | | | |
|---|---|---|---|
| 6,150,663 A | 11/2000 | Rosenthal | |
| 6,165,526 A | 12/2000 | Newman | |
| 6,784,440 B2* | 8/2004 | Fink et al. | 250/435 |
| 7,160,566 B2 | 1/2007 | Fink et al. | |
| 2001/0042842 A1* | 11/2001 | Leighley et al. | 250/504 H |
| 2004/0175290 A1 | 9/2004 | Scheir et al. | |
| 2005/0207152 A1* | 9/2005 | Maxik | 362/231 |
| 2005/0253533 A1* | 11/2005 | Lys et al. | 315/224 |
| 2007/0003430 A1 | 1/2007 | Kaiser et al. | |
| 2007/0141210 A1 | 6/2007 | Kuzmier | |
| 2007/0258851 A1 | 11/2007 | Fogg et al. | |
| 2007/0262734 A1* | 11/2007 | Venkat et al. | 315/360 |
| 2008/0008620 A1* | 1/2008 | Alexiadis | 422/24 |
| 2008/0032010 A1 | 2/2008 | Hankinson et al. | |
| 2009/0012459 A1* | 1/2009 | Sobue et al. | 604/29 |

* cited by examiner

Primary Examiner — Tung X Le

(57) ABSTRACT

The present invention disinfects countertop surfaces using high intensity ultraviolet energy causing photolysis. The light is directed to the working area of an office countertop or the countertop used in food preparation such as in a residential or commercial kitchen. A motion detector provides a mechanism for disabling the light should a pet or individual enter an area during the disinfection process. The device further includes a fluorescent lamp allowing dual functionality wherein the device can provide conventional countertop lighting or disinfection lighting.

3 Claims, 2 Drawing Sheets

COUNTERTOP DECONTAMINATING DEVICE

RELATED APPLICATIONS

This application claims the benefit under 35 U.S.C. 119(e) of U.S. Provisional Patent Application No. 61/098,535, filed Sep. 19, 2009, entitled COUNTERTOP DECONTAMINATION DEVICE, the entirety of which is incorporated herein by reference.

FIELD OF THE INVENTION

This invention is directed to the field of decontamination and in particular to a device for use in decontaminating countertop surfaces such as residential or commercial kitchens, office workspaces, computer keyboards, and the like.

BACKGROUND OF THE INVENTION

It is well known that work surfaces can carry pathogens. Surfaces that are used repeatedly such as office desks, computer keyboards, residential and commercial kitchen countertops carry so many germs that the only reason everyone does not get sick is that many individuals have built a tolerance for such pathogens. While the instant invention can be used for many items, for ease of description this specification will be directed to kitchen countertops which are the last food processing point before food consumption. By the time the food has reached a kitchen, the food has been through a gauntlet of handling, shipping, and refrigeration changes any of which may have exposed the food to harmful pathogens. Food products may include the existence of bacteria, viruses, and other harmful pathogens, it is also well understood that such pathogens thrive in kitchens. The Center for Disease Control estimates that over 75 million food born illnesses occur each year contributing to over 5,000 deaths per year due to food born pathogens. One of the most basic methods of removing pathogens in the kitchen consists of scrubbing the food and countertops with a chlorine wash or other antibacterial and antiviral agent. However, the concern is the surface areas that are used in the final food preparation area may not be decontaminated properly or the use of chemicals may lead to yet another type of contamination. It is impractical to constantly clean a countertop while in the middle of the cooking process and air born pathogens can quickly contaminate a working area. In addition, certain porous working areas, such as cutting blocks are notorious for concealing bacteria and viruses which can quickly contaminate the food. The preparation step may involve cutting a serving portion from a larger portion of a food item, such as a slice of cooked meat product. The preparation step may alternatively involve preparation of multiple smaller size pieces from a food item, such as a vegetable, by an operation such as chopping, dicing, or slicing.

Raw produce may present various bacterial pathogens such as *Shigella* sp., *E. coli* sp. (including *E. coli* O157H7), *Salmonella* sp. Raw meat and processed meat products may present bacterial pathogens such as *E. coli* (including *E. coli* O157: H7), *Salmonella* sp., *Campylobacter jejuni* and *Listeria monocytogenes* and viral pathogens such as Hepatitis A. The levels of these pathogens on produce can often be reduced to a level that will not affect most individuals by rinsing with fresh water shortly before serving. However, residual amounts of pathogen may be transferred to a surface where produce is placed in the food preparation process such as the cutting board.

Thus, what is needed is a decontamination device capable of treating a residential or commercial countertop yet providing a level of safety by use of a motion detector to disable the decontamination light when an individual or pet is within the area.

PRIOR ART

Newman, U.S. Pat. No. 6,165,526 discloses a device where in food is rendered sterile by UV irradiation, preferably with UV at 265.+-.0.15 nm. A sterilization unit may include UV sources and a heat source, which may be a broad band UV source, a source of IR or microwave radiation. Heating prior to UV irradiation can enhance the sterilization, as can rapid cooling after irradiation. Irradiation can also be enhanced by displacing the food during irradiation e.g. by supporting it on a rotatable support and/or by displacing it relative to the support surface.

Fink et al. U.S. Pat. No. 7,160,566 discloses a modular, adjustable, easy to maintain, portable or fixed food sanitation tunnel, which comprises an enclosure for subjecting food to sanitizers including UV light, ozone, hydroperoxides, superoxides and hydroxyl radicals, and a method for using the system. The enclosure includes one or more UV radiation sources and one or more target rods located within a tunnel, such as a c-shaped shell. The UV radiation sources are preferably UV light sources that emit UV light of approximately 185 to 254 nm. Parts of the system are easily removable for cleaning and for maintenance. Also, in an alternative embodiment, the tunnel is located on a frame, and the frame is on wheels.

Scheir et al. U.S. Publication No. 2004/0175290 discloses systems and methods to treat surfaces of food processing machinery and air in a food processing plant. A method of treating a food processing station may include positioning a light emitting treatment system so the output of a germicidal lamp included in the light emitting treatment system will fall on a desired surface of the food processing station. The germicidal lamp of the light emitting treatment system may be energized to emit substantially uniformly distributed ultraviolet radiation across a surface of the food processing station.

Kaiser at al. U.S. Publication No. 2007/0003430 discloses a method of inactivating microorganisms such as viruses within a fluid such as a biological fluid. The method includes the steps of providing a UV reactor, which may take the form of an elongated generally annular reaction chamber surrounding at least one elongated UV lamp, moving the fluid within the reaction chamber in a primary flow directed along the length of the UV lamp, and inducing a circulating secondary flow within the fluid with the secondary flow being superimposed on the primary flow. As the fluid moves through the reaction chamber in the primary flow, it is circulated repeatedly toward and away from the UV lamp in the circulating secondary flow to provide uniform and controllable exposure of the entire volume of fluid to ultraviolet radiation. Microorganisms such as viruses are thus inactivated while desirable components in the fluid, such as proteins, are preserved without the use of a free radical scavenger.

Kuzmier U.S. Publication No. 2007/0141210 discloses a container for perishable food items, such as fruits and vegetables that is provided with a device for producing a substance for killing the fungus or bacteria said substance adhering to the surface of the food item. This substance produced by a device for generating ozone or an oxygen atom and is directly provided in or attached to the food container. A retractable hood can be utilized to prevent the substance from entering the atmosphere of a room prior to the completion of a treatment. A fan is provided for assisting in the introduction as well as the elimination of the substance to and from the interior of the container.

Fogg et al. U.S. Publication No. 2007/0258851 discloses a method for sanitizing and or sterilizing a container or enclosure for use in the food industry or the beverage industry comprising the steps of: providing a container and/or enclosure; providing an electromagnetic radiation source; controllably exposing the container and/or enclosure to electromagnetic radiation from the electromagnetic radiation source for a period of time; and at least one of sanitizing and sterilizing at least a portion of the container and/or enclosure with the electromagnetic radiation.

Alexiadis U.S. Publication No. 2008/0008620 discloses a device including an ultraviolet light source and an additional light source; wherein the additional light source can be a white light fluorescent or an incandescent light; the device is used for sterilizing and cleansing a surface. A switch such as an infrared, movement, electric eye, manual, contact switches, auto or semi-automatic, hard wired, are used to operate the lights. The switch controls the activation and deactivation of the ultraviolet light source and the additional light source such that they are not both on at the same time.

Hankinson et al. U.S. Publication No. 2008/0032010 discloses a system and method for maintaining the integrity of freshly harvested, or freshly cut fruits and vegetables. Specifically, a distinct series of processes which confer a lower total microbial count, delay browning, improve general organoleptic properties, and decrease the amount of chemical contaminants on the exposed surfaces without the use of preservatives. Examples of such process may be applying a first produce integrity maintenance process, a second produce integrity maintenance process, application of an antibrowning agent to the produce by a produce antibrown agent applicator, exposing the produce to ultraviolet light by an ultraviolet light system, and applying an ozone treatment by an ozone treatment system.

SUMMARY OF THE INVENTION

The present invention disinfects using high intensity ultraviolet energy. In general, the present invention includes an ultraviolet (UV) light emitter connected to a base, power connectors and a power control unit that contains an electrical driver system. The UV decontaminates all surfaces by causing photolysis, loss of colony-forming ability (death of microorganism), and inability to support phage growth (enzyme inactivation) and destruction of nucleic acid. This breaking down of organic molecular bonds results in molecular rearrangements and dissociation of the microbe's DNA with cellular damage, which inhibits reproduction.

The device is mounted beneath a hanging cabinet or above a desktop and consists of an ultraviolet light capable of providing disinfection to items placed on the countertop beneath the light. The light is directed to the working area of an office countertop or the countertop used in food preparation such as in a residential or commercial kitchen. For simplicity the examples cited herein will be directed to kitchen countertops. In operation, the food preparing individual may activate the light so as to decontaminate the surface area as well as cause the light to operate at predetermined times under certain conditions. In addition, a motion detector allows for the automatic operation of the light when the food preparer is out of a predetermined range, and disables the light should the an individual reenter the area.

Thus, an objective of the instant invention is to provide a chemical free disinfection device for use in a residential or commercial kitchen capable of decontaminating food preparation areas.

Yet another objective of the instant invention is to provide an ultraviolet light that can be activated upon demand for decontamination of a surface area used for food preparation as well as providing disinfection services during the food preparation stage.

Yet another objective of the instant invention is to provide a device capable of determining if an individual or a pet enters an area during the operation of the ultraviolet light and provide disengagement of the ultraviolet light.

Yet still another objective of the instant invention is to provide a device that can be mounted beneath a cabinet in a residential or commercial kitchen so as to provide disinfection capabilities to a countertop.

Still another objective of the instant invention is to provide a device capable of inhibiting, controlling, and destroying harmful pathogens to allow food products to stay fresh longer and reduce the potential for the harmful effects that can arise from contaminated food.

Yet still another objective of the instant invention is to provide a device at the food preparation point capable of sanitizing food product handlers such as plates and eating utensils.

Yet still another objective of the instant invention is to provide a device at the food preparation point capable of sanitizing computer keyboards.

Yet still another objective of the instant invention is to provide a device capable of sanitizing items placed upon a desktop.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objectives and features thereof.

DETAILED DESCRIPTION OF THE INVENTION

The present invention disinfects countertop surfaces and items placed thereon using high intensity ultraviolet energy. Ultraviolet (UV) light has long been used in the disinfection of water, air, and contact surfaces. The mechanism of disinfection and the effects that UV energy, particularly that in the UVC-germicidal wavelengths, is well understood. In general, the present invention includes an ultraviolet (UV) light emitter connected to a base, power connectors and a power control unit that contains an electrical driver system. The UV decontaminates all surfaces by causing photolysis and destruction of nucleic acid.

Bacteria, molds and viruses substantially absorb UV wavelengths of 210 nm and 310 nm. It is understood that this absorbed UV radiation adversely affects the survivability of many pathogens, such as bacteria, molds and viruses. Commercially available UV lamps can efficiently emit a broad germicidal spectrum that includes these specific wavelengths of UV light, and in the intensity required for effective control. A UV dose of approximately 0.1 joules/cm$^2$ is considered effective in controlling these pathogens. Disinfection is a term that is typically employed to describe the elimination of substantially all pathogens with very few survivors, while the term sterilization is employed to describe the total elimination of all pathogens, without any survivors. The light is directed to the working area of an office countertop or the countertop used in food preparation such as in a residential or commercial kitchen. For simplicity the examples cited herein will be directed to kitchen countertops. For instance, food may be left on a countertop while the individual(s) are eating in another room. During this time airborne bacterial can quickly contaminate the prepared food left on the countertop. Further, leftover food may be saved for later use, if contaminated while on the countertop the contamination will stay with the food when stored. When the food is later reheated, the pathogen can have spoiled the food or grown to such a level that consumption could leave an individual sick.

Figure 1:
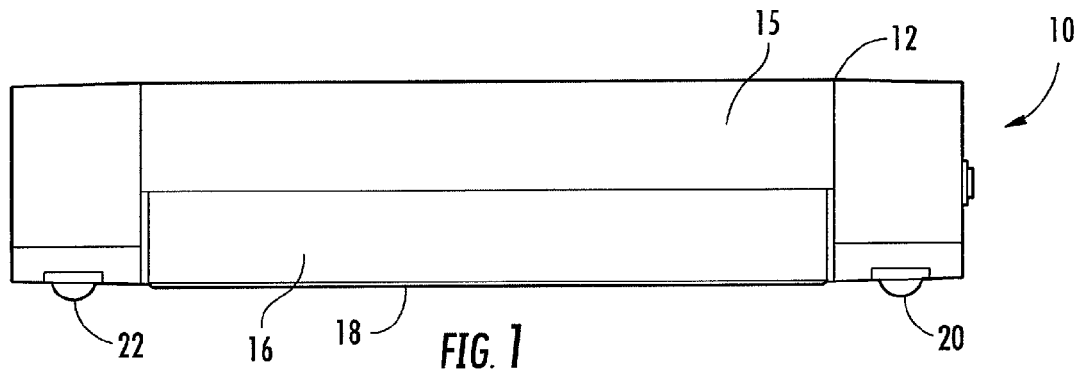
FIG. 1 is a top view of the device.
Figure 2:
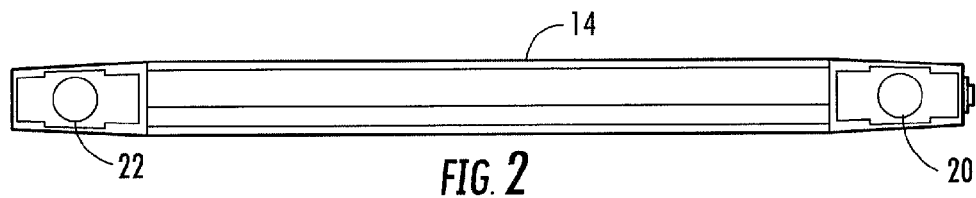
FIG. 2 is a front plane view thereof.
Figure 3:
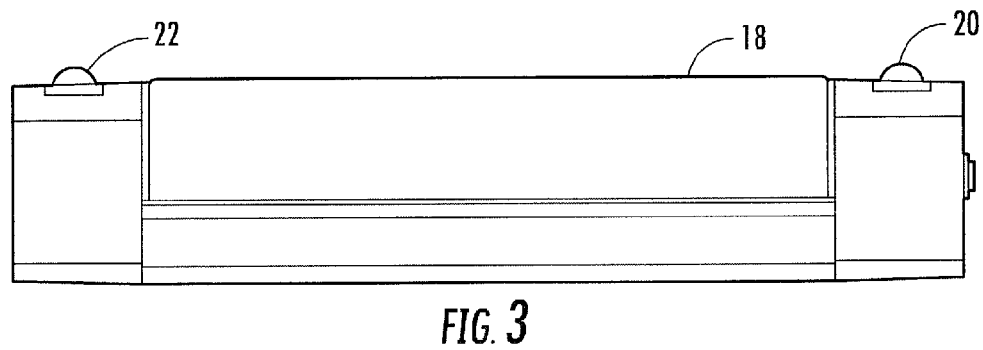
FIG. 3 is a bottom view thereof.
Figure 4:
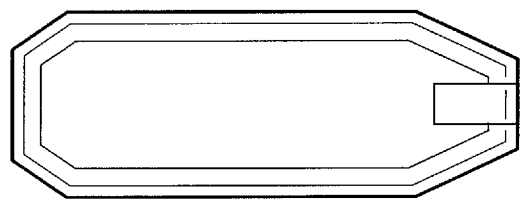
FIG. 4 is a left side view.
Figure 5:
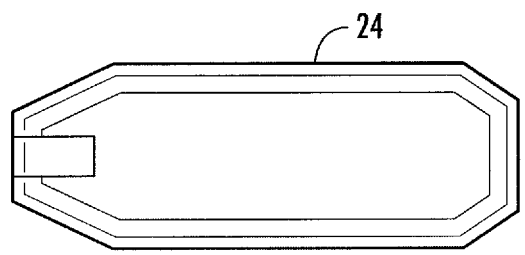
FIG. 5 is a right side view.

Now referring to FIGS. 1-6, the ultraviolet disinfection device (10) of the instant invention includes a housing (12) with a top portion (14) securable to a location beneath a raised cabinet (not shown) in a residential or commercial kitchen. The housing (12) forms an interior for securement of a first ultraviolet light (15) and a second conventional fluorescent light (16). A lens cover (18) is securable to the housing so as to prevent dirt from entering the interior of the housing and employs a directional lens so as to direct the ultraviolet light to be positioned over the countertop while blocking all harmful light from entering the area outside the food processing area. The device is preferably powered by alternating current and includes a first and second motion sensor (20 and 22). An on and off switch (24) controls operation of the device and a control circuitry, FIG. 6, includes an automatic timer (25) for turning off the light after a preset period of time. The lens cover (18) has a greater surface area, as depicted in FIG. 3, so as to provide better illumination over the working area on the countertop. The device can be powered by batteries (30). The batteries are preferably located within the housing, but can also be located externally of the housing.

An important aspect of the present invention is the use of motion sensors that detect the presence of a pet or an individual so as to discontinue operation of the light while in the area. The unit incorporates a parallel internal "on" switch in the form of a motion detector (20, 22). This detector senses the movement of any object within a predefined area. One type of sensor is a passive infrared (PIR) motion sensor, which detects changes in far infrared radiation (8-14 micron wavelength) due to temperature differences between an object (e.g. a human) and its background environment. Upon detection, the motion sensors can disengage the power to the UV light. An exemplary embodiment of the PIR sensor is the pyroelectric detectors which measure changes in infrared radiation. Such detectors operate by the "piezoelectric effect", which causes electrical charge migration in the presence of mechanical strain. Pyroelectric detectors take the form of a capacitor—two electrically conductive plates separated by a dielectric. The dielectric is often a piezoelectric ceramic. When infrared radiation causes a temperature change (and thus some mechanical strain) in the ceramic, electrical charge migrates from one plate to the other. If no external circuit is connected to the detector, then a voltage appears as the "capacitor" charges. If an external circuit is connected between the plates, then a current flows and the UV light is allowed to operate.

Figure 6:
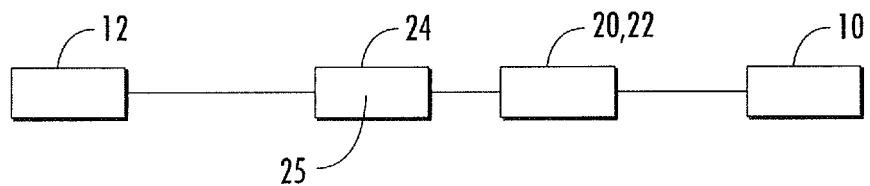
FIG. 6 is a schematic diagram of the electrical control circuit of the present invention.

As illustrated in FIG. 6, on-off switch (24) controls a supply of electrical power from a source of electrical power (12) to the circuitry of the device. An automatic timer shutoff (25) is also used to deactivate the device after a predetermined period of time. The timed shutoff can automatically turn off the power to the UV light after a period of operation, the actual time is adjustable to meet the type of UV employed and the area to be disinfected.

Thus, it is seen that an apparatus for decontaminating countertop surfaces, computer keys boards, and the like devices using UV light is provided. One skilled in the art will appreciate that the present invention can be practiced by other than the preferred embodiments which are presented in this description for the purposes of illustration and not limitation and the present invention is limited only by the claims that follow. It is noted that the equivalents for the particular embodiments in this description may practice the invention as well.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:
1. A countertop ultraviolet disinfection device for placement beneath a raised kitchen cabinet comprising:
a housing securable to the kitchen cabinet;
at least one ultraviolet light positioned within said housing;
at least one fluorescent light secured within said housing;
a source of electrical power, said ultraviolet light and said fluorescent light electrically connected to said source of electrical power;
a directional lens cover secured to said housing and enclosing said ultraviolet light, said directional lens limiting ultraviolet light to a countertop food processing area located in a vicinity of said ultraviolet disinfection device; and
an electrical control circuit including a timer shutoff to deactivate the ultraviolet light after a period of time and at least one pyroelectric motion detector for disconnecting said ultraviolet light from said source of electrical power upon detection of a moving object in the vicinity of said countertop ultraviolet disinfection device.

2. The countertop ultraviolet disinfection device of claim 1 wherein said source of electrical power is at least one battery.

3. The countertop ultraviolet disinfection device of claim 1 wherein said source of power is alternating current.

\* \* \* \* \*